(12) United States Patent
Sakai et al.

(10) Patent No.: US 7,872,136 B2
(45) Date of Patent: Jan. 18, 2011

(54) PROCESS FOR PRODUCTION OF 4-FLUOROISOQUINOLINE-5-SULFONYL HALIDE OR SALT THEREOF

(75) Inventors: Hitoshi Sakai, Nakaniikawa-gun (JP); Masayuki Masumoto, Nakaniikawa-gun (JP); Jyunji Katsuyama, Nakaniikawa-gun (JP); Kazuhiro Onogi, Iruma (JP)

(73) Assignee: Kowa Co., Ltd., Nagoya-shi (JP)

( * ) Notice: Subject to any disclaimer, the term of this patent is extended or adjusted under 35 U.S.C. 154(b) by 694 days.

(21) Appl. No.: 11/816,377

(22) PCT Filed: Feb. 23, 2006

(86) PCT No.: PCT/JP2006/303285
§ 371 (c)(1),
(2), (4) Date: Aug. 15, 2007

(87) PCT Pub. No.: WO2006/090783
PCT Pub. Date: Aug. 31, 2006

(65) Prior Publication Data
US 2009/0209765 A1    Aug. 20, 2009

(30) Foreign Application Priority Data
Feb. 25, 2005    (JP)    ............... 2005-050471

(51) Int. Cl.
*C07D 217/22*    (2006.01)
(52) U.S. Cl. ................................... 546/139
(58) Field of Classification Search .............. None
See application file for complete search history.

(56) References Cited

U.S. PATENT DOCUMENTS

| 5,021,420 A | 6/1991 | Comte et al. |
| 5,036,075 A | 7/1991 | Comte et al. |
| 6,153,608 A | 11/2000 | Hidaka et al. |

FOREIGN PATENT DOCUMENTS

| EP | 0 350 403 A1 | 1/1990 |
| EP | 1 122 254 A2 | 8/2001 |
| JP | 63 2980 | 1/1988 |
| JP | 10 310576 | 11/1998 |
| JP | 2001 520221 | 10/2001 |
| WO | WO 97/28130 | 8/1997 |
| WO | 99 20620 | 4/1999 |
| WO | WO 99/20608 | 4/1999 |

OTHER PUBLICATIONS

Mahindra T. Makhija, et al., "De Novo Design and Synthesis of HIV-1 Integrase Inhibitors", Bioorganic & Medicinal Chemistry, XP002529546, vol. 12, 2004, pp. 2317-2333.
Roger Adams, et al., "Organic Syntheses", Collective vol. I, 1941, 6 Pages.
Marcus S. Morgan, et al., "A Kinetic Study of Alkylation by Ethyl Arylsulfonates", vol. 70, Jan. 1948, pp. 375-378.
Von Emanuel Pfeil, et al., "Production of p-toluenesulfochloride from p-toluenesulfinic acid and copper (II) chloride", Sep. 7, 1949, p. 1 and 183-203 (w/Partial English Translation).
Justine Y. Q. Lai, et al., "Preparation of Substituted Quinolinyl and Isoquinolinyl Sulfonyl Chlorides for the Synthesis of Novel Sulfonamides", Synthetic Communications, vol. 33, No. 19, 2003, pp. 3427-3433.
A. Ricouart, et al., "Design of Potent Protein Kinase Inhibitors Using the Bisubstrate Approach", Journal of Medicinal Chemistry, vol. 34, No. 1, 1991, pp. 73-78.
Georgian, et al., "The Synthesis of 5-Oxoperhydroisoquinolines", Journal of Organic Chemistry, vol. 27, pp. 4571-4579, 1962.
Orita, "Sulfone 0 Mochiiru One-pot Tadankai Han'no", The Chemical Society of Japan Chugoku Shikoku Shibu Kagaku Kondankai, vol. 29th, pp. 39-44, 1998. (with partial English translation).

*Primary Examiner*—Zinna N Davis
(74) *Attorney, Agent, or Firm*—Oblon, Spivak, McClelland, Maier & Neustadt, L.L.P.

(57) ABSTRACT

To provide an effective and simple process for producing 4-fluoroisoquinoline-5-sulfonylhalide or a salt thereof, and a simple method for separating for purification of the product from a by-produced position isomer thereof. The process for producing 4-fluoroisoquinoline-5-sulfonyl halide or a salt thereof, characterized in that the process includes reacting 4-fluoroisoquinoline or a salt thereof with sulfuric anhydride in the presence or absence of sulfuric acid, to thereby form 4-fluoroisoquinoline-5-sulfonic acid or a salt thereof, and, subsequently, reacting the formed sulfonic acid compound with a halogenating reagent.

18 Claims, No Drawings

PROCESS FOR PRODUCTION OF 4-FLUOROISOQUINOLINE-5-SULFONYL HALIDE OR SALT THEREOF

CONTINUING DATA

This application is a 371 of PCT/JP2006/303285 filed Feb. 23, 2006.

TECHNICAL FIELD

The present invention relates to a process for producing 4-fluoroisoquinoline-5-sulfonyl halide or a salt thereof, which is an important production intermediate for pharmaceuticals.

BACKGROUND ART (S)-(−)-1-(4-Fluoroisoquinolin-5-yl)sulfonyl-2-methyl-1,4-homopiperazine hydrochloride is a compound which is represented by the following formula (1);

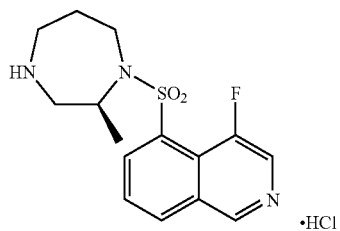

(1)

and which is known to be a useful prophylactic and therapeutic agent for cerebrovascular disorders such as cerebral infarction, cerebral hemorrhage, subarachnoidal hemorrhage, and cerebral edema, particularly a suppressor for cerebrovascular spasm such as cerebral stroke (see Patent Document 1).

In the synthesis of compound (1), 4-fluoroisoquinoline-5-sulfonyl chloride represented by formula (2a):

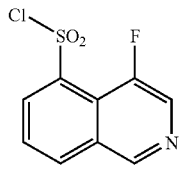

(2a)

or a salt thereof is known to be an important intermediate (Patent Document 1).

For reactions to form an aromatic sulfonyl chloride, approaches such as acid-halogenation of sulfonic acid in which an aromatic ring is sulfonated with fuming sulfuric acid, and the sulfonated ring is reacted with phosphorus pentachloride or phosphorus oxychloride (see Non-Patent Document 1); chlorosulfonylation employing chlorosulfuric acid (see Non-Patent Document 2); reaction between sulfinic acid and chlorine or a chloride (see Non-Patent Document 3); synthesis from a diazonium salt; chlorination of a thiol or disulfide (i.e., sulfone derivative in a low oxidation state) in an aqueous solution; trapping a Grignard reagent or an organic lithium reagent with sulfuryl chloride; and Friedel-Craft reaction employing sulfuryl chloride and a Lewis acid have been known.

Among these approaches, some are employed also for producing a variety of isoquinolinesulfonyl chlorides. For example, chlorosulfonylation employing chlorosulfuric acid (see Non-Patent Document 4), acid-halogenation of sulfonic acid (see Non-Patent Document 5), and synthesis from a diazonium salt (see Patent Document 2) are employed in practice.

However, only a limited number of approaches have been reported for production of 4-fluoroisoquinoline-5-sulfonyl halide, and all the reported approaches are based on synthesis from a diazonium salt (see Patent Documents 1 and 3 to 5). Among these documents, Patent Document 1 discloses the sole known approach employing the following scheme.

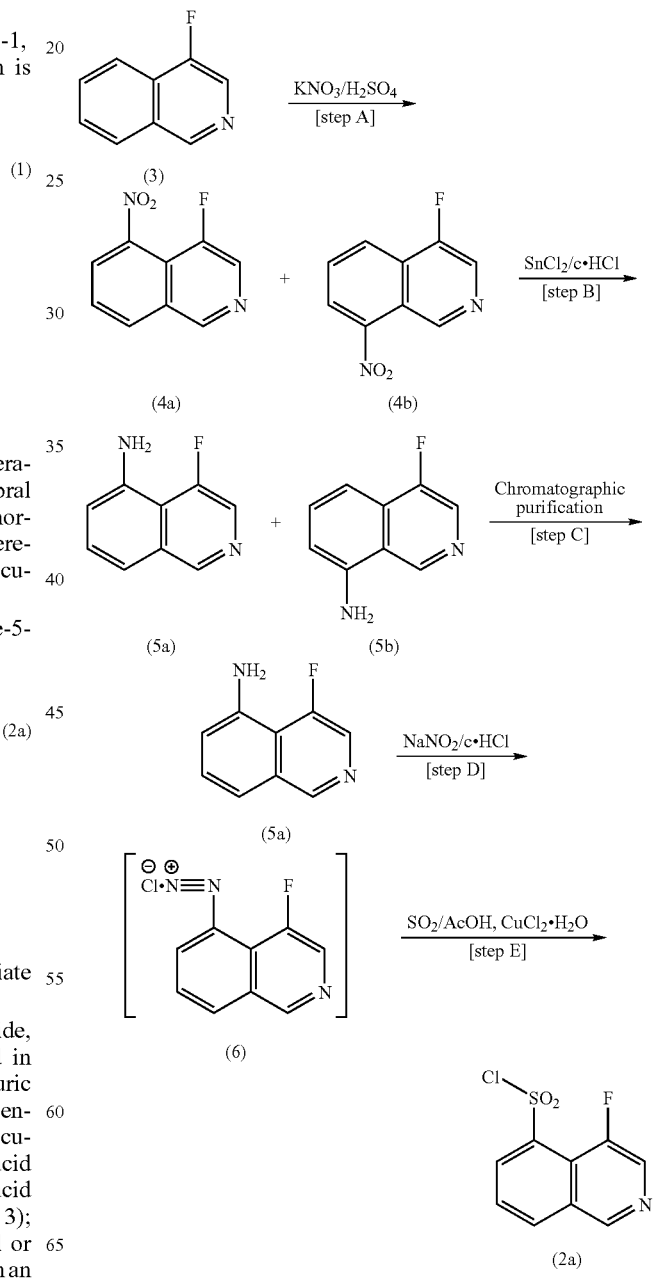

Specifically, 4-fluoroisoquinoline (3) is nitrified with potassium nitrate in sulfuric acid, to thereby form 4-fluoro-5-nitroisoquinoline (4a) and a position isomer (4b) thereof [step A]. Subsequently, these two products are reduced by use of concentrated hydrochloric acid and stannous chloride dihydrate, to thereby form 4-fluoro-5-aminoisoquinoline (5a) and a position isomer (5b) thereof [step B]. 5-Amino-4-fluoroisoquinoline (5a) is separated through column chromatography for purification [step C]. The purified product is diazotized with sodium nitrite [step D]. The diazo compound is subjected to Sandmeyer reaction employing $SO_2$ gas-saturated acetic acid and cupric chloride dihydrate [step E], to thereby yield 4-fluoroisoquinoline-5-sulfonyl chloride (2a).

In the aforementioned reaction scheme, the synthesis of compound (2a) from compound (3) requires five steps in total, the steps including chromatographic purification and a step of producing an unstable diazonium salt. Therefore, there has been demand for a production process which realizes more direct and effective introduction of a sulfonyl halide group into the 5-position of isoquinoline through simple operation.

[Patent Document 1] International Laid-Open WO99/20620

[Patent Document 2] EP No. 350403

[Patent Document 3] EP No. 1122254

[Patent Document 4] International Laid-Open WO99/54306

[Patent Document 5] International Laid-Open WO97/28130

[Non-Patent Document 1] Org. Synth., I, 84(1941)

[Non-Patent Document 2] J. Amer. Chem. Soc., 70, 375(1948)

[Non-Patent Document 3] Ann., 565, 203(1949)

[Non-Patent Document 4] Synthetic Communications, 33(19), 3427(2003)

[Non-Patent Document 5] J. Med. Chem., 34(1), 73(1991)

DISCLOSURE OF THE INVENTION

Problems to be Solved by the Invention

Thus, an object of the present invention is to provide an effective and simple process for producing 4-fluoroisoquinoline-5-sulfonyl halide or a salt thereof. Another object of the invention is to provide a simple method for separating for purification of the product from a by-produced position isomer thereof.

Means for Solving the Problems

In view of the foregoing, the present inventors have conducted extensive studies, and have found that 4-fluoroisoquinoline-5-sulfonyl halide or a salt thereof can be produced by reacting 4-fluoroisoquinoline or a salt thereof with sulfuric anhydride in the presence or absence of sulfuric acid, to thereby form 4-fluoroisoquinoline-5-sulfonic acid or a salt thereof, and reacting the product with a halogenating reagent; that, through continuously and sequentially performing these reactions, 4-fluoroisoquinoline-5-sulfonyl halide or a salt thereof can be produced in "one pot"; and that the formed crude target product is reacted with acid, to thereby form an acid-added target product, whereby the target product can be separated for purification from a by-produced position isomer without performing any operation that employs a column. The present invention has been accomplished on the basis of these findings.

Accordingly, the present invention provides a process for producing 4-fluoroisoquinoline-5-sulfonyl halide or a salt thereof, characterized in that the process comprises reacting 4-fluoroisoquinoline or a salt thereof with sulfuric anhydride in the presence or absence of sulfuric acid, to thereby form 4-fluoroisoquinoline-5-sulfonic acid, and, subsequently, reacting the formed sulfonic acid compound with a halogenating reagent.

EFFECTS OF THE INVENTION

According to the process for producing 4-fluoroisoquinoline-5-sulfonyl halide of the present invention, the synthesis can be performed in "one pot," and the target product is yielded in the form of acid-added salt. Therefore, the product can be readily separated from a by-produced position isomer and purified, whereby the process can be carried out in a simple manner at high efficiency. Thus, the production process of the present invention can reduce production cost, and also, shorten production time.

BEST MODES FOR CARRYING OUT THE INVENTION

According to the present invention, 4-fluoroisoquinoline-5-sulfonyl halide (2) can be produced through the following scheme:

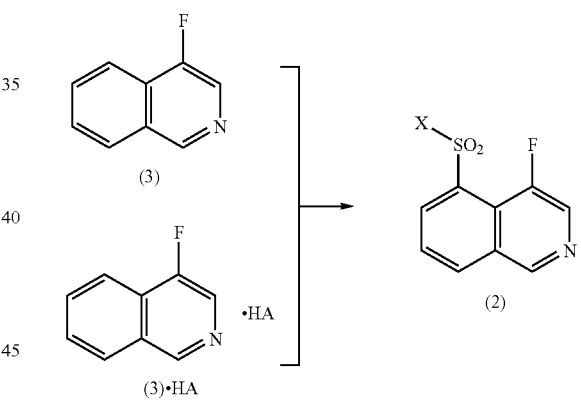

(wherein X represents a halogen atom, and A represents an acid residue)

including reacting 4-fluoroisoquinoline (3) or a salt thereof with sulfuric anhydride in the presence or absence of sulfuric acid, to thereby form 4-fluoroisoquinoline-5-sulfonic acid or a salt thereof [step 1], and, subsequently, reacting the formed sulfonyl halide compound with a halogenating reagent [step 2].

In the above reaction scheme, examples of the halogen atom X include chlorine, bromine, and iodine, and examples of the acid residue A include residues of inorganic acids such as sulfuric acid, hydrochloric acid, nitric acid, hydrobromic acid, and phosphoric acid; and residues of organic acids such as acetic acid, trifluoroacetic acid, oxalic acid, fumaric acid, maleic acid, tartaric acid, and tosylic acid.

[Step 1]

4-Fluoroisoquinoline (3), which is a starting material, may be produced through the method disclosed in the pamphlet of WO 99/20620. A salt of 4-fluoroisoquinoline (3) may be produced through treating 4-fluoroisoquinoline (3) with an acid of interest in a solvent.

Examples of the acid employed in the treatment include the same inorganic acids and organic acid as mentioned above. Of these, inorganic acids are preferred, with sulfuric acid being particularly preferred.

Examples of the solvent employed in the treatment include ketones such as acetone; ethers such as ether, tetrahydrofuran, and dioxane; esters such as ethyl acetate; chlorine-containing solvents such as methylene chloride; aromatic hydrocarbons such as benzene and toluene; and alcohols such as methanol and ethanol. Of these, acetone, ether, tetrahydrofuran, and dioxane are preferred, with acetone and ether being more preferred.

The acid is preferably used in an amount of 1 to 1.5 mol with respect to 1 mol of 4-fluoroisoquinoline (3), more preferably in an amount of 1 to 1.1 mol. The acid itself or a solution in which the acid is dissolved may be used.

In sulfonation, 4-fluoroisoquinoline (3) or a salt thereof is reacted with sulfuric anhydride in the presence or absence of sulfuric acid. When sulfuric acid is added to the reaction, sulfuric acid is preferably used in an amount of 1.5 mol to 5 mol with respect to 1 mol of 4-fluoroisoquinoline (3) or a salt thereof, more preferably in an amount of 2 mol to 2.5 mol.

Sulfuric anhydride is preferably used in an amount of 5 mol to 15 mol with respect to 1 mol of 4-fluoroisoquinoline (3) or a salt thereof, more preferably in an amount of 8 mol to 10 mol.

Since the reaction between 4-fluoroisoquinoline (3) or a salt thereof and sulfuric acid is exothermic, preferably, the reaction system is cooled externally so as to maintain the internal temperature at 10° C. to 40° C.

When sulfuric anhydride is added to the reaction system, the internal temperature is preferably 10° C. to 70° C., more preferably 30° C. to 50° C. After addition of sulfuric anhydride, the reaction is preferably performed at an internal temperature of 10° C. to 60° C., more preferably 20° C. to 40° C.

The reaction time is preferably 5 hours to 30 hours, more preferably 10 hours to 15 hours.

4-Fluoroisoquinoline-5-sulfonic acid or a salt thereof produced in step 1 may be used in the subsequent step without isolating from the reaction mixture.

[Step 2]

In step 2, acid-halogenation includes adding a halogenating reagent to the reaction mixture produced in step 1, followed by heating.

Examples of the halogenating reagent employed in the reaction include thionyl halides such as thionyl chloride and thionyl bromide; and phosphorus halides such as phosphorus oxychloride and phosphorus pentachloride. Among them, thionyl chloride and thionyl bromide are preferred, with thionyl chloride being more preferred.

The halogenating reagent is preferably used in an amount of 2 mol to 10 mol with respect to 1 mol of 4-fluoroisoquinoline (3) or a salt thereof, more preferably in an amount of 4 mol to 6 mol.

When the halogenating reagent is added to the reaction system, the internal temperature is preferably 10° C. to 70° C., more preferably 20° C. to 40° C. After addition of the halogenating reagent, the reaction is preferably performed at an internal temperature of 40° C. to 100° C., more preferably 60° C. to 80° C.

The reaction time is preferably 0.2 hours to 7 hours, more preferably 1 hour to 4 hours.

The thus-formed 4-fluoroisoquinoline-5-sulfonyl halide (2) can be separated as an acid-added salt from a by-produced position isomer for purification. Specifically, the reaction mixture is alkalinized with a base in the presence of an organic solvent and water, and an acid of interest is added to the formed organic layer, whereby the acid-added salt can be separated.

Examples of the solvent employed in the above treatment include chlorine-containing solvents such as methylene chloride and chloroform; ethers such as ether, tetrahydrofuran, and dioxane; esters such as ethyl acetate; aromatic hydrocarbons such as benzene and toluene; and alcohols such as methanol and ethanol. Of these, methylene chloride, chloroform, and ethyl acetate are more preferred. These solvents are preferably used in an amount of 1 mL to 1,000 mL with respect to 1 g of 4-fluoroisoquinoline-5-sulfonyl halide (2), more preferably 5 mL to 150 mL.

Examples of the base employed in the treatment include inorganic bases such as sodium carbonate, potassium carbonate, sodium hydrogencarbonate, potassium hydrogen carbonate, sodium hydroxide, and potassium hydroxide; and organic bases such as triethylamine and diisopropylethylamie. Of these, sodium hydrogencarbonate and potassium hydrogencarbonate are preferred.

The pH during extraction with an organic solvent is preferably 7.5 to 9.5, more preferably 7.5 to 8.5.

Examples of the acid employed in the reaction include inorganic acids such as hydrochloric acid, hydrobromic acid, sulfuric acid, and nitric acid; and lower fatty acids such as acetic acid and propionic acid; and organic acids such as p-toluenesulfonic acid. Of these, hydrochloric acid is particularly preferred. Although no particular limitation is imposed on the form of acid for forming an acid-added salt, a solution of the acid dissolved in an organic solvent is preferably used. The acid is preferably used in an amount of 1 mol to 2 mol with respect to 1 mol of 4-fluoroisoquinoline-5-sulfonyl halide (2), more preferably 1.1 mol to 1.5 mol.

The temperature at which the acid-added salt is formed is preferably 0° C. to the boiling point of the used solvent, depending on the solvent employed.

EXAMPLES

The present invention will next be described in detail by way of examples, which should not be construed as limiting the invention thereto.

Example 1

Production of 4-fluoroisoquinoline-5-sulfonyl chloride hydrochloride from 4-fluoroisoquinoline To a 10-L-capacity reactor equipped with a stirrer, a thermometer, a condenser, and a dropper, 4-fluoroisoquinoline (750.0 g, 5.1 mol) which has been produced according to the method disclosed in the pamphlet of WO 99/20620 was placed. While internal temperature of the reactor was maintained at 10° C. to 30° C. under cooling with stirring, concentrated sulfuric acid (1,100 g, 11.2 mol) was added dropwise thereto. After completion of addition, the bath temperature was elevated to 40° C., and the mixture was stirred for 0.5 hours. Subsequently, under cooling and stirring, sulfuric anhydride (3,577.7 g, 44.69 mol as $SO_3$) was added dropwise little by little to the reactor through a dropping funnel which had been maintained at 40° C., while the internal temperature of the reactor was maintained at 30° C. to 45° C., and the mixture was stirred at room temperature for 12 hours. After termination of reaction, thionyl chloride (3,296.7 g, 27.7 mol) was added dropwise little by little, while the internal temperature was maintained at 25° C. to 35° C., and the reaction mixture was stirred with heating at an internal temperature of 70° C. for 2.5 hours. After completion of reaction, under cooling and stirring, the reaction mixture was added dropwise to a mixture of ice-water (55 L) and methylene chloride (40 L), while the internal temperature was maintained at −7° C. to −1° C. Sodium hydrogencarbonate (14.5 kg) was added little by little to the reaction mixture under stirring, to thereby adjust the pH of the aqueous layer to 8. The precipitated solid was removed through filtration, and the solid was washed with methylene chloride. The wash liquid was combined with the filtrate, and the mixture was transferred to a separating funnel, whereby an organic layer was collected. The organic layer was washed with water and dried by use of sodium sulfate anhydrate. After removal of sodium sulfate anhydrate through filtration, 4N HCl/EtOAc (1,500 mL) was added to the filtrate (45 L) under stirring. Through one hour stirring, the precipitated crystals were collected through filtration and washed with isopropyl ether (2 L), followed by drying at room temperature under reduced pressure, to thereby yield 786.6 g of pale brown crystals (55%) The crystals were suspended in methylene chloride (24 L), and the product crystals were converted to a free form by use of a saturated sodium hydrogencarbonate aqueous solution (4 L). The formed organic layer was collected and washed with saturated brine, followed by drying by use of sodium sulfate anhydrate. After removal of the drying agent through filtration, from the organic layer, methylene chloride was added thereto so as to adjust the total volume to 35 L, and the free form was converted again to the corresponding hydrochloride form by use of 4N HCl/EtOAc (750 mL), while the internal temperature was maintained at 21° C. to 26° C. As a result, 585.6 g of the title compound was yielded as pale yellow crystals (40.7%). The ratio in relative amount of the title compound to the 8-position isomer in the crystals as determined through HPLC was 99.68:0.32.

mp: 199.7 to 201.0° C. (d)

IR (KBr) cm$^{-1}$: 2994, 2310, 2086, 1955, 1655, 1495, 1375, 1355, 1214, 1181, 892, 777, 762.

$^1$H-NMR (400 MHz, DMSO-d$_6$) δ: 9.63 (1H, s), 8.77 (1H, d, J=4.80 Hz), 8.67 (1H, d, J=7.79 Hz), 8.48 (1H, d, J=7.79 Hz), 7.94 (1H, dd, J=7.79, 7.79 Hz)

Example 2

Production of 4-fluoroisoquinoline sulfuric acid salt

4-Fluoroisoquinoline (9.40 kg, 63.9 mol) was dissolved in acetone (35 L). Under stirring, sulfuric acid (6.58 kg, 67.1 mol) was added little by little carefully to the solution, while the internal temperature was maintained at 5±5° C., followed by stirring for two hours. The precipitated crystals were collected through filtration and washed with acetone (28 L), followed by drying under reduced pressure, to thereby yield 15.5 kg of 4-fluoroisoquinoline sulfuric acid salt (98.8%).

mp: 165.7 to 167.0° C.

IR (KBr) cm$^{-1}$: 1659, 1617, 1601, 1558, 1506, 1407, 1377, 1288, 1245, 1225, 1145, 1069, 1025, 893, 867, 795, 781, 714.

$^1$H-NMR (400 MHz, DMSO-d$_6$) δ: 9.59 (1H, s), 9.07 (2H, brs), 8.78 (1H, d, J=3.20 Hz), 8.49 (1H, d, J=7.79 Hz), 8.27 (1H, d, J=7.79 Hz), 8.16 (1H, dd, J=7.79, 7.79 Hz), 8.01 (1H, dd, J=7.79, 7.79 Hz)

Example 3

Production of 4-fluoroisoquinoline-5-sulfonyl chloride hydrochloride from 4-fluoroisoquinoline sulfuric acid salt To a 200-mL-capacity reactor equipped with a stirrer, a thermometer, a condenser, and a dropper, sulfuric anhydride (94.3 g, 1.18 mol) which had been liquefied through heating at 20° C. to 35° C. was added, and the internal temperature was adjusted to 26° C. to 34° C. While the internal temperature was maintained, 4-fluoroisoquinoline sulfuric acid salt (33.33 g, 0.136 mol) produced in Example 2 was gradually added to the reactor. Thereafter, the internal temperature of the reactor was adjusted to 30° C., and the content was stirred for 13 hours. Thionyl chloride (89.0 g, 0.75 mol) was added dropwise to the reaction mixture, followed by heating to 70° C. and stirring for four hours. After completion of reaction, the reactor was cooled.

Water (333 mL), ice (600 g), and methylene chloride (500 mL) were added to another reactor (capacity: 3 L), and the reactor was cooled to 0° C. or lower. While the internal temperature was carefully controlled so as not to exceed 5° C., the reaction mixture was gradually added dropwise to the reactor. Subsequently, sodium hydrogencarbonate (330 g) was gradually added to the mixture while the internal temperature was maintained at 5° C. to 10° C., and the formed inorganic salt was removed through filtration. The filtrate was separated, and the aqueous layer was extracted with methylene chloride (333 mL). Collected organic layers were combined, and the combined organic layer was washed with saturated brine (166 mL), followed by drying through addition of sodium sulfate anhydrate (21 g) to the washed layer. After removal of the drying agent through filtration, methylene chloride was added to the organic layer so as to adjust the total volume to 1.2 L. Then, 4N HCl/EtOAc (41 mL) was added dropwise to the organic layer at 18 to 21° C., followed by stirring at 30° C. for one hour. The precipitated crystals were collected through filtration and washed with methylene chloride (110 mL), to thereby yield 17.42 g of 4-fluoroisoquinoline-5-sulfonyl chloride hydrochloride (45.4%) as white crystals. The ratio in relative amount of the title compound to the 8-position isomer in the crystals as determined through HPLC was 99.64:0.36.

The invention claimed is:

1. A process for producing 4-fluoroisoquinoline-5-sulfonyl halide or a salt thereof, comprising reacting 4-fluoroisoquinoline or a salt thereof with sulfuric anhydride in the presence or absence of sulfuric acid, to thereby form 4-fluoroisoquinoline-5-sulfonic acid or a salt thereof, and, subsequently, reacting the 4-fluoroisoquinoline-5-sulfonic acid or a salt thereof with a halogenating reagent.

2. The process as described in claim 1, wherein the salt of 4-fluoroisoquinoline is a 4-fluoroisoquinoline sulfuric acid salt.

3. The process for producing 4-fluoroisoquinoline-5-sulfonyl halide or a salt thereof as described in claim 1 or 2, wherein the formed 4-fluoroisoquinoline-5-sulfonic acid or a salt thereof which has not been subjected to isolation is reacted with a halogenating reagent.

4. The process as described in claim 1 or 2, wherein the 4-fluoroisoquinoline-5-sulfonyl halide or a salt thereof is 4-fluoroisoquinoline-5-sulfonyl chloride or a salt thereof.

5. A process for producing 4-fluoroisoquinoline-5-sulfonyl halide hydrochloride, wherein the process comprises reacting 4-fluoroisoquinoline-5-sulfonyl halide formed by the process as recited in claim 1 or 2 with hydrochloric acid and collecting the product in the form of a hydrochloride salt.

6. The process for producing 4-fluoroisoquinoline-5-sulfonyl halide or a salt thereof as described in claim 1, wherein the 4-fluoroisoquinoline or a salt thereof is reacted with sulfuric anhydride in the presence of sulfuric acid.

7. The process for producing 4-fluoroisoquinoline-5-sulfonyl halide or a salt thereof as described in claim 1, wherein the 4-fluoroisoquinoline or a salt thereof is reacted with sulfuric anhydride in the absence of sulfuric acid.

8. The process for producing 4-fluoroisoquinoline-5-sulfonyl halide or a salt thereof as described in claim 1, wherein sulfuric acid is used in an amount of 1.5 to 5 mol with respect to 1 mol of 4-fluoroisoquinoline or a salt thereof.

9. The process for producing 4-fluoroisoquinoline-5-sulfonyl halide or a salt thereof as described in claim 1, wherein sulfuric acid is used in an amount of 2 to 2.5 mol with respect to 1 mol of 4-fluoroisoquinoline or a salt thereof.

10. The process for producing 4-fluoroisoquinoline-5-sulfonyl halide or a salt thereof as described in claim 1, wherein sulfuric anhydride is used in an amount of 5 to 15 mol with respect to 1 mol of 4-fluoroisoquinoline or a salt thereof.

11. The process for producing 4-fluoroisoquinoline-5-sulfonyl halide or a salt thereof as described in claim 1, wherein sulfuric anhydride is used in an amount of 8 to 10 mol with respect to 1 mol of 4-fluoroisoquinoline or a salt thereof.

12. The process for producing 4-fluoroisoquinoline-5-sulfonyl halide or a salt thereof as described in claim 1, wherein the formed 4-fluoroisoquinoline-5-sulfonic acid or a salt thereof is not isolated prior to reaction with the halogenating agent.

13. The process for producing 4-fluoroisoquinoline-5-sulfonyl halide or a salt thereof as described in claim 1, wherein the halogenating agent is a thionyl halide or phosphorous halide.

14. The process for producing 4-fluoroisoquinoline-5-sulfonyl halide or a salt thereof as described in claim 1, wherein the halogenating agent is phosphorous oxychloride or phosphorous pentachloride.

15. The process for producing 4-fluoroisoquinoline-5-sulfonyl halide or a salt thereof as described in claim 1, wherein the halogenating agent is thionyl bromide.

16. The process for producing 4-fluoroisoquinoline-5-sulfonyl halide or a salt thereof as described in claim 1, wherein the halogenating agent is thionyl chloride.

17. The process for producing 4-fluoroisoquinoline-5-sulfonyl halide or a salt thereof as described in claim 1, wherein the halogenating agent is used in an amount of 2 to 10 mol with respect to 1 mol of 4-fluoroisoquinoline or a salt thereof.

18. The process for producing 4-fluoroisoquinoline-5-sulfonyl halide or a salt thereof as described in claim 1, wherein the halogenating agent is used in an amount of 4 to 6 mol with respect to 1 mol of 4-fluoroisoquinoline or a salt thereof.

\* \* \* \* \*